(12) United States Patent
Harada et al.

(10) Patent No.: US 6,881,863 B2
(45) Date of Patent: Apr. 19, 2005

(54) PROCESS FOR PRODUCING 2-HALOGENOCYCLOALKANONE OXIME

(75) Inventors: Katsumasa Harada, Ube (JP); Yasuhisa Fukuda, Ube (JP); Yoshinori Yamanaka, Ube (JP)

(73) Assignee: Ube Industries, Ltd., Ube (JP)

( * ) Notice: Subject to any disclaimer, the term of this patent is extended or adjusted under 35 U.S.C. 154(b) by 0 days.

(21) Appl. No.: 10/468,880

(22) PCT Filed: Feb. 21, 2002

(86) PCT No.: PCT/JP02/01515

§ 371 (c)(1),
(2), (4) Date: Aug. 20, 2003

(87) PCT Pub. No.: WO02/066419

PCT Pub. Date: Aug. 29, 2002

(65) Prior Publication Data

US 2004/0073064 A1 Apr. 15, 2004

(30) Foreign Application Priority Data

Feb. 21, 2001 (JP) ..................................... 2001-044566

(51) Int. Cl.[7] ..................... C07C 251/44; C07C 249/12; C07B 61/00

(52) U.S. Cl. ...................................... 564/253; 564/267

(58) Field of Search ................................. 564/253, 267

(56) References Cited

U.S. PATENT DOCUMENTS 4,746,707 A   5/1988  Fiedler et al.

FOREIGN PATENT DOCUMENTS

DE   1 205 089 A   11/1965
FR   1 442 416 A    6/1966

OTHER PUBLICATIONS

Genas et al., Bull. Chim. Soc. Fr., (1965), 10, p. 2833–2842.*

English language translation of the International Preliminary Examination Report in PCT/JP02/01515.

* cited by examiner

Primary Examiner—Brian Davis
(74) Attorney, Agent, or Firm—Frishauf, Holtz, Goodman & Chick, P.C.

(57) ABSTRACT

The present invention relates to a process for preparing 2-halogenocycloalkanone oxime which comprises subjecting a 2-halogenocycloalkenone oxime compound to reduction with hydrogen in the presence of a platinum-carried catalyst.

8 Claims, No Drawings

PROCESS FOR PRODUCING 2-HALOGENOCYCLOALKANONE OXIME

This application is a 371 of PCT/JP02/01515 filed Feb. 21, 2002.

TECHNICAL FIELD

The present invention relates to a process for preparing a 2-halogenocycloalkanone oxime by selectively reducing carbon-carbon double bond(s) of a 2-halogenocycloalkenone oxime compound which is contacted with hydrogen in the presence of a platinum-carried catalyst. According to the process of the present invention, for example, 2-halogenocyclododecanone oxime which becomes an intermediate for preparing 1,10-dicyanodecane or 1,12-diaminododecane can be prepared from 2-halogenocyclododecadienone oxime in good yield. 1,10-dicyanodecane or 1,12-diaminododecane is a compound useful as a starting material for Nylon 12.

BACKGROUND ART

As a prior art relating to the present invention, for example, in German (DE) Patent No. 11 62 359, Angewandte Chemie International Edition in English (Angew. Chem. Int. Ed. Eng.), 2688 (1963), Chim. Ind. (Milan), 46, 875 (1964), German (DE) Patent No. 12 05 089, Bulletin de la Societe Chimique de France (Bull. Soc. Chim. Fr.), 10, 2833 (1965), Italian (IT) Patent No. 720514, Journal für Practische Chemie (J. Pract. Chem.), 33, 282 (1966), Japanese Patent Publications No. Sho. 43-16124 and Sho. 44-3815, there are description about hydrogen reduction of 2-halogenocycloalkenone oxime compounds including 2-chlorocyclododecadienone oxime using a palladium catalyst. However, main products in these reactions are cycloalkanone oxime in which not only carbon-carbon double bond(s) but also a chloro group are also reduced.

Also, in Bull. Soc. Chim. Fr., 10, 2833 (1965), an example of obtaining 2-chlorocyclododecanone oxime from 2-chlorocyclododecadienone oxime using platinum oxide has been described but the yield is extremely low as 10%, so that it is not satisfied. Also, since a platinum oxide catalyst is dissolved during the reaction, so that there is a problem that it's recovery and reuse are not so easy.

Thus, the halogen group of the 2-halogenocycloalkenone oxime compound is extremely easily reduced, so that it has not been known a method of selectively reducing carbon-carbon double bond(s) of the 2-halogenocycloalkenone oxime compound in good yield.

An object of the present invention is to solve the above-mentioned problems and to provide a process for preparing a 2-halogenocycloalkanone oxime in high yield by selectively reducing carbon-carbon double bond(s) of a 2-halogenocycloalkenone oxime compound with good efficiency.

DISCLOSURE OF THE INVENTION

The present invention relates to a process for preparing a 2-halogenocycloalkanone oxime by subjecting a 2-halogenocycloalkenone oxime compound to reduction with hydrogen in the presence of a platinum-carried catalyst.

BEST MODE FOR CARRYING OUT THE INVENTION

In the following, the present invention is explained in detail.

The present invention can be shown by the following formula (1):

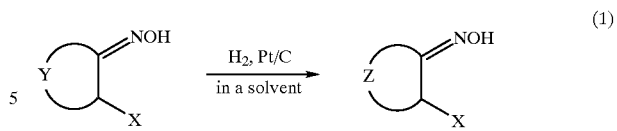

wherein X represents a halogen atom, Y represents an unsaturated alkylene group having one or more carbon-carbon double bond(s), and Z represents a saturated alkylene group.

The 2-halogenocycloalkenone oxime compound which is a starting compound of the present invention can be synthesized by the reaction of a corresponding alkene compound and a nitrosyl halide, etc., and the like. For example, preparation of 2-chlorocyclododecadienone oxime can be carried out by the method described in La Chimica E L'induskia (Chim. Ind. (Milan)), 49 (5), 494 (1967).

As the 2-halogenocycloalkenone oxime compound to be used in the present invention, there may be preferably mentioned those comprising cyclic hydrocarbon having 5 to 12 carbon atoms and having one or more carbon-carbon double bond(s). More preferably, it is 2-halogenocyclododecadienone oxime having 12 carbon atoms, further preferably 2-halogeno-5,9-cyclododecadienone oxime.

Incidentally, a stereospecific structure of a carbon-carbon double bond of the 2-halogenocycloalkenone oxime compound may be any form such as cis or trans. Also, these isomers may be used in admixture.

As the 2-halogenocycloalkenone oxime compound, a commercially available product or a synthesized product may be used as they are, or those purified by crystallization, etc., may be used.

The halogen atom in the 2-halogenocycloalkenone oxime compound is preferably a fluorine atom, a chlorine atom, a bromine atom and an iodine atom, more preferably a chlorine atom.

As the 2-halogenocycloalkenone oxime compound, there may be specifically mentioned 2-chlorocyclopentenone oxime, 2-chlorocyclohexenone oxime, 2-chlorocycloheptenone oxime, 2-chlorocyclooctenone oxime, 2-chlorocyclononenone oxime, 2-chlorocyclodecenone oxime, 2-chlorocycloundecenone oxime, 2-chlorocyclododecenone oxime, 2-chlorocyclododecadienone oxime and the like. It is preferably 2-chlorocyclododecadienone oxime, particularly preferably 2-chloro-5,9-cyclododecadienone oxime. These may be used singly or in combination of two or more kinds in admixture.

The platinum-carried catalyst to be used in the reaction of the present invention is a heterogeneous catalyst such as a solid catalyst in which a platinum element or a compound containing a platinum element is carried on an inactive carrier, and the like, preferably a powder catalyst, more preferably a powder catalyst having an average particle size of several $\mu m$ to several hundreds $\mu m$ further 1 $\mu m$ to 500 $\mu m$. As the above-mentioned inactive carrier, there may be mentioned activated charcoal, alumina, silica, silica alumina, zeolite, spinel, etc., preferably activated charcoal, alumina, silica, silica alumina, more preferably activated charcoal. As the compound containing a platinum element to be used in the present invention, there may be mentioned, for example, platinum chloride, chloroplatinic acid, platinum hydroxide, platinum sulfide, platinum oxide, etc. As the platinum-carried catalyst in the present invention, that in which a platinum element is carried on activated charcoal is preferably used. Also, an amount of the platinum element to be carried on an inactive carrier is preferably 0.1 to 30% by weight, more preferably 0.5 to 10% by weight based on the amount of the inactive carrier. The platinum element in the catalyst may be carried on the surface or inside of the inactive carrier or both of them.

An amount of the platinum-carried catalyst to be used is not specifically limited, and it is preferably used in an amount that a molar ratio of the platinum element to the 2-halogenocycloalkenone oxime compound as the starting material is 1/3 to 1/50000.

As the reaction solvent in the present invention, an organic solvent is usually used. As the organic solvent, it is not specifically limited so long as it is inactive to the present reaction, and there may be mentioned an aliphatic ester such as methyl acetate, ethyl acetate, etc., an aliphatic alcohol such as methanol, ethanol, etc., a nitrile such as acetonitrile, propionitrile, etc., an aliphatic halogenated hydrocarbon such as methylene chloride, carbon tetrachloride, etc., an ether such as diethyl ether, dioxane, etc., an aliphatic hydrocarbon such as hexane, heptane, etc., an aromatic hydrocarbon such as benzene, toluene, chlorobenzene, etc., and an aliphatic carboxylic acid such as acetic acid, propionic acid, etc. There may be preferably mentioned an aliphatic ester such as methyl acetate, ethyl acetate, etc., and an aliphatic carboxylic acid such as acetic acid, propionic acid, etc. An amount of these solvents to be used is generally 1 to 100-fold weight, preferably 3 to 50-fold weight based on the amount of the 2-halogenocycloalkenone oxime compound.

In the present invention, a method of reducing the 2-halogenocycloalkenone oxime compound with hydrogen is generally carried out in a hydrogen gas atmosphere by mixing an organic solvent, the 2-halogenocycloalkenone oxime compound and the platinum-carried catalyst.

A hydrogen pressure at the reaction is generally carried out under normal pressure, and may be carried out under pressure.

A pressure in the reaction under pressure is not specifically limited, and judging from an endurable pressure of the reaction apparatus or a yield of the objective material, it is preferably 100 atm or lower, more preferably 60 atm or lower.

A reaction temperature is not specifically limited so long as it is a boiling point or lower of the reaction solvent to be used, and it is generally carried out at 0 to 100° C., preferably 10 to 80° C., more preferably 10 to 50° C.

When the hydrogen pressure at the reaction and the reaction temperature are too low, they are not preferred since the reaction required too long time and further the yield of the objective material is lowered. Also, when the hydrogen pressure at the reaction and the reaction temperature are too high, they are also not preferred since reduction proceeds excessively and there occur tendency that the yield of the objective material is also lowered.

A reaction apparatus is also not specifically limited and it is carried out with a reactor equipped with a usual stirring device.

Reaction time may vary depending on the reaction conditions such as the above-mentioned concentration, temperature, etc., and it is usually carried out for 0.5 to 24 hours.

The 2-halogenocycloalkanone oxime obtained by the present invention can be separated and purified by distillation, crystallization, etc.

EXAMPLE

Next, the present invention is explained specifically by referring to Examples.

Example 1

In 10 ml of ethyl acetate were dissolved 1.0 g (4.4 mmol) of 2-chloro-5,9-cyclododecadienone oxime and 0.46 g (0.022 mmol) of 2 wt % platinum/C catalyst (containing 52.71% of water), and under hydrogen atmosphere, the mixture was stirred under normal pressure and room temperature (25° C.) for 6 hours.

Here, 2 wt % platinum/C catalyst means 2 wt % platinum/ activated charcoal carried catalyst.

After completion of the reaction, the catalyst was removed by filtration, and the resulting reaction solvent was quantitatively analyzed by liquid chromatography (HPLC). As a result, it was found that 0.88 g (3.8 mmol, yield: 86%) of 2-chlorocyclododecanone oxime had been formed. The results are shown in Table 1.

Analytical results by various apparatuses of 2-chlorocyclododecanone oxime obtained as a white solid after evaporation of the solvent are as mentioned below.

(1) Mass spectrometric analysis (MS) m/z (EI): 231, 196m/z (CI): 232 (MH$^+$) (2) Proton nuclear magnetic resonance analysis ($^1$H-NMR)

$^1$H-NMR (300 MHz, CDCl$_3$) δ: 1.22 to 1.45 (14H, m), 1.59 to 1.70 (2H, m), 1.88 to 1.96 (1H,m), 2.29 to 2.45 (2H, m), 2.76 to 2.86 (1H, m), 4.56 to 4.62 (1H, m), 8.00 to 8.58 (1H, m) (3) Melting point 106.6 to 107.2° C.

Comparative Examples 1 and 2

The reaction was carried out in the same manner as in Example 1 except for using 0.0062 g (0.022 mmol) of PtO$_2$·3H$_2$O (Comparative example 1) and 0.117 g (0.022 mmol) of 2 wt % Pd/C catalyst (Comparative example 2) in place of 2 wt % platinum/C catalyst (containing 52.71% of water) (referred to as 2 wt % Pt/C in the table). The results are also shown in Table 1.

In either of the comparative examples, conversions were both low and the objective compound could not be obtained.

TABLE 1

| | Reaction conditions | | | | | |
|---|---|---|---|---|---|---|
| | | | | Reaction temperature (° C.) | Reaction conditions | |
| | CLOX g (mmol) | Catalyst g (mmol) | Solvent ml | Reaction time (hr) | CLOX Conversion (%) | CLOX12 Yield (%) |
| Example 1 | 1.0 (4.4) | 2 wt % Pt/C 0.46 (0.022) | AcOEt 10 ml | 25° C. 6 hr | 100 | 86 |
| Comparative example 1 | 1.0 (4.4) | PtO$_2$·3H$_2$O 0.0062 (0.022) | AcOEt 10 ml | 25° C. 6 hr | 12 | 0 |

TABLE 1-continued

| | Reaction conditions | | | | Reaction conditions | |
|---|---|---|---|---|---|---|
| | CLOX g (mmol) | Catalyst g (mmol) | Solvent ml | Reaction temperature (° C.) Reaction time (hr) | CLOX Conversion (%) | CLOX12 Yield (%) |
| Comparative example 2 | 1.0 (4.4) | 2 wt % Pd/C 0.117 (0.022) | AcOEt 10 ml | 25° C. 6 hr | 5 | 0 |

Common conditions
CLOX 1.0 g (4.4 mmol),
Catalyst/CLOX molar ratio = 1/200
Hydrogen pressure: Normal pressure,
Reaction time: 6 hours,
Reaction temperature: 25° C.
CLOX; 2-Chloro-5,9-cyclododecadienone oxime
CLOX12; 2-Chlorocyclododecanone oxime
AtOEt; Ethyl acetate

Example 2

The reaction was carried out in the same manner as in Example 1 except for subjecting to filtration after the reaction of Example 1 and by using a recovered 2 wt % platinum/C catalyst to investigate the lifetime of the catalyst. As a result, 2-chlorocyclododecanone oxime was obtained with a yield of 95%.

These results are shown in Table 2.

TABLE 2

| | Reaction conditions | | | | Reaction conditions | |
|---|---|---|---|---|---|---|
| | CLOX g (mmol) | Catalyst g (mmol) | Solvent ml | Reaction temperature (° C.) Reaction time (hr) | CLOX Conversion (%) | CLOX12 Yield (%) |
| Example 1 | 1.0 (4.4) | 2 wt % Pt/C 0.46 (0.022) | AcOEt 10 ml | 25° C. 6 hr | 100 | 86 |
| Example 2 | 1.0 (4.4) | Recovered catalyst of Example 1 2 wt % Pt/C 0.46 (0.022) | AcOEt 10 ml | 25° C. 6 hr | 100 | 95 |

Common conditions
CLOX 1.0 g (4.4 mmol),
Catalyst/CLOX molar ratio = 1/200
Hydrogen pressure: Normal pressure,
Reaction time: 6 hours,
Reaction temperature: 25° C.
CLOX; 2-Chloro-5,9-cyclododecadienone oxime
CLOX12; 2-Chlorocyclododecanone oxime
AcOEt; Ethyl acetate

Examples 3 and 4

The reaction was carried out in the same manner as in Example 1 except for changing the solvent to acetic acid (Example 3) and toluene (Example 4). The results are shown in Table 3.

TABLE 3

|  | CLOX g (mmol) | Catalyst g (mmol) | Solvent ml | Reaction conditions Reaction temperature (° C.) Reaction time (hr) | Reaction conditions CLOX Conversion (%) | CLOX12 Yield (%) |
|---|---|---|---|---|---|---|
| Example 1 | 1.0 (4.4) | 2 wt % Pt/C 0.46 (0.022) | AcOEt 10 ml | 25° C. 6 hr | 100 | 86 |
| Example 3 | 1.0 (4.4) | 2 wt % Pt/C 0.46 (0.022) | AcOH 10 ml | 25° C. 7 hr | 100 | 97 |
| Example 4 | 1.0 (4.4) | 2 wt % Pt/C 0.46 (0.022) | Toluene 10 ml | 25° C. 9 hr | 93 | 47 |

Common conditions
CLOX 1.0 g (4.4 mmol),
Catalyst/CLOX molar ratio = 1/200
Hydrogen pressure: normal pressure,
Reaction temperature: 25° C.
CLOX; 2-Chloro-5,9-cyclododecadienone oxime
CLOX12; 2-Chlorocyclododecanone oxime
AcOEt; Ethyl acetate
AcOH; Acetic acid Examples 5 and 6

The reaction was carried out in the same manner as in Example 1 except for changing the molar ratio of the catalyst to 2-chloro-5,9-cyclododecadienone oxime to 1/1000, a hydrogen pressure to 60 kg/cm$^2$, and a reaction temperature to 60° C. (Example 5) and 80° C. (Example 6). The results are shown in Table 4.

TABLE 4

|  | CLOX g (mmol) | Catalyst g (mmol) | Solvent ml | Reaction conditions Reaction temperature (° C.) Reaction time (hr) | Reaction conditions CLOX Conversion (%) | CLOX12 Yield (%) |
|---|---|---|---|---|---|---|
| Example 5 | 1.0 (4.4) | 2 wt % Pt/C 0.09 (0.0044) | AcOEt 10 ml | 60° C. 6 hr | 100 | 81 |
| Example 6 | 1.0 (4.4) | 2 wt % Pt/C 0.09 (0.0044) | AcOEt 10 ml | 80° C. 6 hr | 100 | 81 |

Common conditions
CLOX 1.0 g (4.4 mmol),
Catalyst/CLOX molar ratio = 1/1000
Hydrogen pressure: 60 kg/cm$^2$,
Reaction time: 6 hours
CLOX; 2-Chloro-5,9-cyclododecadienone oxime
CLOX12; 2-Chlorocyclododecanone oxime
AcOEt; Ethyl acetate Utilizability in Industry According to the present invention, the 2-halogenocycloalkanone oxime can be obtained in high yield. Also, the catalyst is not dissolved during the reaction, so that it can be easily recovered by a means such as filtration, etc., whereby recovery and reuse of the catalyst can be carried out easily.

What is claimed is:

1. A process for preparing 2-halogenocycloalkanone oxime which comprises subjecting a 2-halogenocycloalkenone oxime compound to reduction with hydrogen in the presence of a platinum-carried catalyst.

2. The process for preparing 2-halogenocycloalkanone oxime according to claim 1, wherein the platinum-carried catalyst is a heterogenous catalyst in which a platinum element or a compound containing a platinum element is carried on an inactive support selected from an activated charcoal, alumina, silica and silica alumina.

3. The process for preparing 2-halogenocycloalkanone oxime according to claim 1, wherein the platinum-carried catalyst is a catalyst in which a platinum element is carried on an activated charcoal.

4. The process for preparing 2-halogenocycloalkanone oxime according to claim 1, wherein the 2-halogenocycloalkenone oxime compound is 2-halogenocyclododecadienone oxime.

5. The process for preparing 2-halogenocycloalkanone oxime according to claim 2, wherein the platinum-carried catalyst is a catalyst in which a platinum element is carried on an activated charcoal.

6. The process for preparing 2-halogenocycloalkanone oxime according to claim 2, wherein the 2-halogenocycloalkenone oxime compound is 2-halogenocyclododecadienone oxime.

7. The process for preparing 2-halogenocycloalkanone oxime according to claim 3, wherein the 2-halogenocycloalkenone oxime compound is 2-halogenocyclododecadienone oxime.

8. The process for preparing 2-halogenocycloalkanone oxime according to claim 5, wherein the 2-halogenocycloalkenone oxime compound is 2-halogenocyclododecadienone oxime.

* * * * *